US012600764B2

(12) United States Patent
Luan et al.

(10) Patent No.: US 12,600,764 B2
(45) Date of Patent: Apr. 14, 2026

(54) ANTIGEN-BINDING PROTEINS TARGETING CORONAVIRUS (COV) VARIANTS

(71) Applicant: International Business Machines Corporation, Armonk, NY (US)

(72) Inventors: Binquan Luan, Chappaqua, NY (US); Leili Zhang, Yorktown Heights, NY (US); Tien Huynh, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1266 days.

(21) Appl. No.: 17/459,486

(22) Filed: Aug. 27, 2021

(65) Prior Publication Data

US 2023/0073821 A1     Mar. 9, 2023

(51) Int. Cl.
C07K 16/10          (2006.01)
C07K 14/005         (2006.01)

(52) U.S. Cl.
CPC ........ C07K 16/1003 (2023.08); C07K 14/005 (2013.01); *C07K 2317/55* (2013.01); *C07K 2317/56* (2013.01); *C07K 2317/565* (2013.01)

(58) Field of Classification Search
CPC .............. C07K 14/005; C07K 16/1003; C07K 2317/55; C07K 2317/56; C07K 2317/565
See application file for complete search history.

(56) References Cited

U.S. PATENT DOCUMENTS

| | | | |
|---|---|---|---|
| 10,954,289 B1 | 3/2021 | Babb et al. | |
| 2009/0137002 A1* | 5/2009 | Petrul | C07K 16/2866 |
| | | | 435/69.6 |
| 2021/0070887 A1 | 3/2021 | Ambrogelly et al. | |
| 2021/0269520 A1* | 9/2021 | Allan | A61P 19/02 |
| 2021/0292393 A1 | 9/2021 | Westendorf et al. | |

FOREIGN PATENT DOCUMENTS

| | | | | |
|---|---|---|---|---|
| CN | 11349150 B | 2/2020 | | |
| WO | WO-2011140151 A1 * | 11/2011 | ......... | C07K 16/2863 |
| WO | 2017147293 A1 | 8/2017 | | |
| WO | 2019224717 A2 | 11/2019 | | |
| WO | 2019224718 A2 | 11/2019 | | |
| WO | WO-2021163031 A1 * | 8/2021 | ............. | C07K 16/00 |
| WO | WO-2021183195 A1 * | 9/2021 | ....... | G01N 33/56983 |
| WO | WO-2021183359 A1 * | 9/2021 | ........... | A61K 39/215 |
| WO | 2023/026246 A1 | 3/2023 | | |

OTHER PUBLICATIONS

Sela-Culang (Frontiers in Immunology (2013) 4: 302) (Year: 2013).*
Genheden (Expert Opinion Drug Discovery (2015) 10(5): 449-461) (Year: 2015).*

Dondelinger (Frontiers in Immunology (2018) 9: 2278) (Year: 2018).*
Almagro (Frontiers in Immunology (2018) 8: 1751) (Year: 2018).*
"P01861—IGHG4_HUMAN" entry on Uniprot. Sequence of "P01861-2" (v2) last updated on May 3, 2023. Accessed at <https://www.uniprot.org/uniprotkb/P01861/entry> on Apr. 22, 2025. (Year: 2023).*
Ni (The Protein Journal (2024) 43: 683-696) (Year: 2024).*
Liu (MAbs (2021) 13(1): e1919285) (Year: 2021).*
B. Luan and T. Huynh, "Insights on SARS-CoV-2's Mutations for Evading Human Antibodies: Sacrifice and Survival," bioRxiv, Posted Feb. 7, 2021, https://doi.org/10.1101/2021.02.06.430088.
B. Jones et al., "The neutralizing antibody, LY-CoV555, protects against SARS-COV-2 infection in non-human primates," Science Translational Medicine, Apr. 5, 2021. doi: 10.1126/scitranslmed.abf1906.
K. Westendorf et al., "LY-CoV1404 potently neutralizes SARS-CoV-2 variants," bioRxiv, Posted May 4, 2021, https://doi.org/10.1101/2021.04.30.442182.
S. Robinson et al., "Epitope profiling of coronavirus-binding antibodies using computational structural modelling," bioRxiv, Posted Apr. 12, 2021.
H. Cho et al., "Ultrapotent bispecific antibodies neutralize emerging SARS-CoV-2 variants," bioRxiv, Posted Apr. 1, 2021, https://doi.org/10.1101/2021.04.01.437942.
P. Taylor et al., "Neutralizing monoclonal antibodies for treatment of COVID-19." Nat Rev Immunol, 2021. https://doi.org/10.1038/s41577-021-00542-x.
L.G. Abinader (Oct. 28, 2020) U.S. Government funding of Lilly's LY-CoV555 antibody against COVID-19. Knowledge Ecology International. https://www.keionline.org/34308.
U.S. Food & Drug Administration (Apr. 16, 2021) Coronavirus (COVID-19) Update: FDA Revokes Emergency use Authorization for Monoclonal Antibody Bamlanivimab. https://www.fda.gov/news-events/press-announcements/coronavirus-covid-19-update-fda-revokes-emergency-use-authorization-monoclonal-antibody-bamlanivimab.
T. Starr et al.; "Complete map of SARS-CoV-2 RBD mutationsthat escape the monoclonal antibodyLY-CoV555 and its cocktail with LY-CoV016". Cell Report Medicine, 2, 100255, 2021.
T. Tada et al.; "Decreased neutralization of SARS-CoV-2 global variants by therapeutic anti-spike protein monoclonal antibodies". bioRxiv, doi: https://doi.org/10.1101/2021.02.18.431897.

(Continued)

*Primary Examiner* — Brad Duffy
*Assistant Examiner* — Elizabeth A Shupe
(74) *Attorney, Agent, or Firm* — Amin, Turocy & Watson, LLP

(57) ABSTRACT

Techniques regarding antigen-binding proteins that can bind to CoV (e.g., SARS-CoV-2) variants are provided. For example, one or more embodiments described herein can comprise an antigen-binding protein that can comprise a heavy polypeptide chain variable region with an amino acid sequence that is a variant of SEQ ID NO: 7. The amino acid sequence can comprise at least one amino acid substitution selected from the group consisting of: R50D, R50E, R50W, R50F, R50Y, R50L, R50V, R50I, R50Pho, I54D, I54E, I54W, I54F, I54Y, I54Pho, L55D, L55E, L55W, L55F, L55Y, and L55Pho.

14 Claims, 10 Drawing Sheets

Specification includes a Sequence Listing.

(56)                    References Cited

OTHER PUBLICATIONS

J. Villar et al.; "Dexamethasone treatment for the acute respiratory distress syndrome: a multicentre, randomised controlled trial". The Lancet Respiratory Medicine 2020, 8, 267-276.

J. Beigel et al.; "Remdesivir for the treatment of Covid-19—preliminary report". New England Journal of Medicine 2020.

L. Piroth et al.; "Comparison of the Characteristics, Morbidity, and Mortality of COVID-19 and Seasonal Influenza: a Nationwide, Population-Based Retrospective Cohort Study". Lancet Respir. Med. 2020, 9, 251-259.

Coronaviridae Study Group of the International Committee on Taxonomy of Viruses, The Species Severe Acute Respiratory Syndrome-Related Coronavirus: Classifying 2019-nCOV and Naming it SARS-CoV-2. Nat. Microbio. 2020, 5, 536.

International Search Report and Written Opinion for International Application No. PCT/IB2022/058006 dated Dec. 1, 2022.

Liu, et al., "Structure-Function Analysis of Resistance to Bamlanivimab by SARS-CoV-2 Variants Kappa, Delta, and Lambda," J. Chem. Inf. Model. Oct. 14, 2021, 61, 5133-5140, https://doi.org/10.1021/acs.jcim.1c01058.

Zhang, et al., "in silico Assessment of Antibody Drug Resistance to Bamlanivimab of SARS-CoV-2 Variant B.1.617," May 14, 2021, Paper in collection COVID-19 SARS-CoV-2 preprints from medRxiv and bioRxiv, doi: https://doi.org/10.1101/2021.05.12.443826.

Jones et al., "LY-CoV555, a rapidly isolated potent neutralizing antibody, provides protection in a non-human primate model of SARS-CoV-2 infection", Science Translational Medicine, Oct. 9, 2020, 29 pages.

* cited by examiner

RBD of SARS-COV-2 Spike Protein

TNLCPF GEVFNATRFA SVYAWNRKRI SNCVADYSVL

YNSASFSTFK CYGVSPTKLN DLCFTNVYAD SFVIRGDEVR QIAPGQTGKI

ADYNYKLPDD FTGCVIAWNS NNLDSKVGGN YNYLYRLFRK SNLKPFERDI

STEIYQAGST PCNGVEGFNC YFPLQSYGFQ PTNGVGYQPY RVVVLSFELL

HAPATVCGP (SEQ ID NO: 1)

RBD of SARS-COV-2 Spike Protein with E484K Amino Acid Substitution

TNLCPF GEVFNATRFA SVYAWNRKRI SNCVADYSVL

YNSASFSTFK CYGVSPTKLN DLCFTNVYAD SFVIRGDEVR QIAPGQTGKI

ADYNYKLPDD FTGCVIAWNS NNLDSKVGGN YNYLYRLFRK SNLKPFERDI

STEIYQAGST PCNGVKGFNC YFPLQSYGFQ PTNGVGYQPY RVVVLSFELL

HAPATVCGP (SEQ ID NO: 2)

RBD of SARS-COV-2 Spike Protein with E484Q Amino Acid Substitution

TNLCPF GEVFNATRFA SVYAWNRKRI SNCVADYSVL

YNSASFSTFK CYGVSPTKLN DLCFTNVYAD SFVIRGDEVR QIAPGQTGKI

ADYNYKLPDD FTGCVIAWNS NNLDSKVGGN YNYLYRLFRK SNLKPFERDI

STEIYQAGST PCNGVQGFNC YFPLQSYGFQ PTNGVGYQPY RVVVLSFELL

HAPATVCGP (SEQ ID NO: 3)

FIG. 1

RBD of SARS-COV-2 Spike Protein with L452R Amino Acid Substitution

TNLCPF GEVFNATRFA SVYAWNRKRI SNCVADYSVL

YNSASFSTFK CYGVSPTKLN DLCFTNVYAD SFVIRGDEVR QIAPGQTGKI

ADYNYKLPDD FTGCVIAWNS NNLDSKVGGN YNYRYRLFRK SNLKPFERDI

STEIYQAGST PCNGVEGFNC YFPLQSYGFQ PTNGVGYQPY RVVVLSFELL

HAPATVCGP (SEQ ID NO: 4)

RBD of SARS-COV-2 Spike Protein with L452Q Amino Acid Substitution

TNLCPF GEVFNATRFA SVYAWNRKRI SNCVADYSVL

YNSASFSTFK CYGVSPTKLN DLCFTNVYAD SFVIRGDEVR QIAPGQTGKI

ADYNYKLPDD FTGCVIAWNS NNLDSKVGGN YNYQYRLFRK SNLKPFERDI

STEIYQAGST PCNGVEGFNC YFPLQSYGFQ PTNGVGYQPY RVVVLSFELL

HAPATVCGP (SEQ ID NO: 5)

FIG. 2

RBD of SARS-COV-2 Spike Protein with E484K and L452R Amino Acid Substitutions

TNLCPF GEVFNATRFA SVYAWNRKRI SNCVADYSVL

YNSASFSTFK CYGVSPTKLN DLCFTNVYAD SFVIRGDEVR QIAPGQTGKI

ADYNYKLPDD FTGCVIAWNS NNLDSKVGGN YNYRYRLFRK SNLKPFERDI

STEIYQAGST PCNGVKGFNC YFPLQSYGFQ PTNGVGYQPY RVVVLSFELL

HAPATVCGP (SEQ ID NO: 6)

FIG. 3

Fab V<sub>H</sub> of *Bamlanivimab*

QVQLVQSGAEVKKPGSSVKVSCKASGGTFSNYAISWVRQAPGQGLEWMGRIIPILGIANYAQKFQGRVTITADK
STSTAYMELSSLRSEDTAVYYCARGYYEARHYYYYYAMDVWGQGTAVTVSSASTKGPSVFPLAPCSRSTSEST
AALGCLVKDYFPEPVTVSWNSGALTSGVHTFPAVLQSSGLYSLSSVVTVPSSSLGTKTYTCNVDHKPSNTKVDK
RVHHHHHH        (SEQ ID NO: 7)

| Amino Acid Substitution | Amino Acid Sequence | ID |
|---|---|---|
| R50D | QVQLVQSGAEVKKPGSSVKVSCKASGGTFSNYAISWVRQAPGQGLEWMGDIIPI LGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 9 |
| R50E | QVQLVQSGAEVKKPGSSVKVSCKASGGTFSNYAISWVRQAPGQGLEWMGEIIPI LGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 10 |
| R50W | QVQLVQSGAEVKKPGSSVKVSCKASGGTFSNYAISWVRQAPGQGLEWMGWIIP ILGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 11 |
| R50F | QVQLVQSGAEVKKPGSSVKVSCKASGGTFSNYAISWVRQAPGQGLEWMGFIIPI LGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 12 |
| R50Y | QVQLVQSGAEVKKPGSSVKVSCKASGGTFSNYAISWVRQAPGQGLEWMGYIIPI LGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 13 |
| R50L | QVQLVQSGAEVKKPGSSVKVSCKASGGTFSNYAISWVRQAPGQGLEWMGLIIPI LGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 14 |
| R50V | QVQLVQSGAEVKKPGSSVKVSCKASGGTFSNYAISWVRQAPGQGLEWMGVIIPI LGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 15 |
| R50I | QVQLVQSGAEVKKPGSSVKVSCKASGGTFSNYAISWVRQAPGQGLEWMGIIIPI LGIANYAQKFQGRVTITADKSTSTAYMELSSLRSEDTAVYYCARGYYEARHYY YYYAMDVWGQGTAVTVSSASTKGPSVFPLAPCSRSTSESTAALGCLVKDYFPEP VTVSWNSGALTSGVHTFPAVLQSSGLYSLSSVVTVPSSSLGTKTYTCNVDHKPS NTKVDKRVHHHHHH | SEQ ID NO: 16 |

FIG. 4

Fab V<sub>L</sub> of *Bamlanivimab*

DIQMTQSPSSLSASVGDRVTITCRASQSISSYLSWYQQKPGKAPKLLIYAASSLQSGVPSRFSGS
GSGTDFTLTITSLQPEDFATYYCQQSYSTPRTFGQGTKVEIKRTVAAPSVFIFPPSDEQLKSGTA
SVVCLLNNFYPREAKVQWKVDNALQSGNSQESVTEQDSKDSTYSLSSTLTLSKADYEKHKV
YACEVTQGTTSVTKSFNRGEC    (SEQ ID NO: 8)

| Amino Acid Substitution | Amino Acid Sequence | ID |
|---|---|---|
| R96D | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPDTFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 17 |
| R96E | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPETFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 18 |
| R96W | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPWTFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 19 |
| R96F | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPFTFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 20 |
| R96Y | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPYTFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 21 |
| R96L | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPLTFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 22 |
| R96V | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPVTFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 23 |
| R96I | DIQMTQSPSSLSASVGDRVTITCRASQSISSYLSWYQQKPGKAPKLLIYAASSLQ SGVPSRFSGSGSGTDFTLTITSLQPEDFATYYCQQSYSTPITFGQGTKVEIKRTVA APSVFIFPPSDEQLKSGTASVVCLLNNFYPREAKVQWKVDNALQSGNSQESVTE QDSKDSTYSLSSTLTLSKADYEKHKVYACEVTQGTTSVTKSFNRGEC | SEQ ID NO: 24 |

FIG. 5

Fab V<sub>H</sub> of _Bamlanivimab_

QVQLVQSGAEVKKPGSSVKVSCKASGGTFSNYAISWVRQAPGQGLEWMGRIIPILGIANYAQKFQGRVTITADKS
TSTAYMELSSLRSEDTAVYYCARGYYEARHYYYYYAMDVWGQGTAVTVSSASTKGPSVFPLAPCSRSTSESTAA
LGCLVKDYFPEPVTVSWNSGALTSGVHTFPAVLQSSGLYSLSSVVTVPSSSLGTKTYTCNVDHKPSNTKVDKRVH
HHHHH          (SEQ ID NO: 7)

| Amino Acid Substitution | Amino Acid Sequence | ID |
|---|---|---|
| I54D | QVQLVQSGAEVKKPGSSVKVSCKASGGTFSNYAISWVRQAPGQGLEWMGRIIPDL GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 25 |
| I54E | QVQLVQSGAEVKKPGSSVKVSCKASGGTFSNYAISWVRQAPGQGLEWMGRIIPEL GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 26 |
| I54W | QVQLVQSGAEVKKPGSSVKVSCKASGGTFSNYAISWVRQAPGQGLEWMGRIIPWL GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 27 |
| I54F | QVQLVQSGAEVKKPGSSVKVSCKASGGTFSNYAISWVRQAPGQGLEWMGRIIPFL GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 28 |
| I54Y | QVQLVQSGAEVKKPGSSVKVSCKASGGTFSNYAISWVRQAPGQGLEWMGRIIPYL GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 29 |

FIG. 6

Fab V<sub>H</sub> of *Bamlanivimab*

QVQLVQSGAEVKKPGSSVKVSCKASGGTFSNYAISWVRQAPGQGLEWMGRIIPILGIANYAQKFQGRVTITADKS
TSTAYMELSSLRSEDTAVYYCARGYYEARHYYYYYAMDVWGQGTAVTVSSASTKGPSVFPLAPCSRSTSESTAA
LGCLVKDYFPEPVTVSWNSGALTSGVHTFPAVLQSSGLYSLSSVVTVPSSSLGTKTYTCNVDHKPSNTKVDKRVH
HHHHH          (SEQ ID NO: 7)

| Substitution | Amino Acid Sequence | ID |
|---|---|---|
| L55D | QVQLVQSGAEVKKPGSSVKVSCKASGGTFSNYAISWVRQAPGQGLEWMGRIIPID GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 30 |
| L55E | QVQLVQSGAEVKKPGSSVKVSCKASGGTFSNYAISWVRQAPGQGLEWMGRIIPIE GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 31 |
| L55W | QVQLVQSGAEVKKPGSSVKVSCKASGGTFSNYAISWVRQAPGQGLEWMGRIIPIW GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 32 |
| L55F | QVQLVQSGAEVKKPGSSVKVSCKASGGTFSNYAISWVRQAPGQGLEWMGRIIPIF GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 33 |
| L55Y | QVQLVQSGAEVKKPGSSVKVSCKASGGTFSNYAISWVRQAPGQGLEWMGRIIPIY GIANYAQKFQGRVTITADKSTSTAYMELSSLRSEDTAVYYCARGYYEARHYYYY YAMDVWGQGTAVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSNTKV DKRVHHHHHH | SEQ ID NO: 34 |

FIG. 7

Table 1

| Complex | MMGBSA binding free energy (kcal/mol) |
|---|---|
| *Bamlanivimab* + RBD-E484 (WT) | -157.87 |
| *Bamlanivimab* + RBD-K484 | -108.24 |
| *Bamlanivimab*-EE + RBD-K484 | -156.79 |

CONTACTING AN ANTIGEN-BINDING PROTEIN WITH THE RBD OF A SARS-COV-2 SPIKE PROTEIN VARIANT CARRYING THE E484K,Q MUTATION

902

INHIBITING THE ABILITY OF THE SARS-COV-2 SPIKE PROTEIN VARIANT FROM BINDING TO A RECEPTOR

Figure 10:
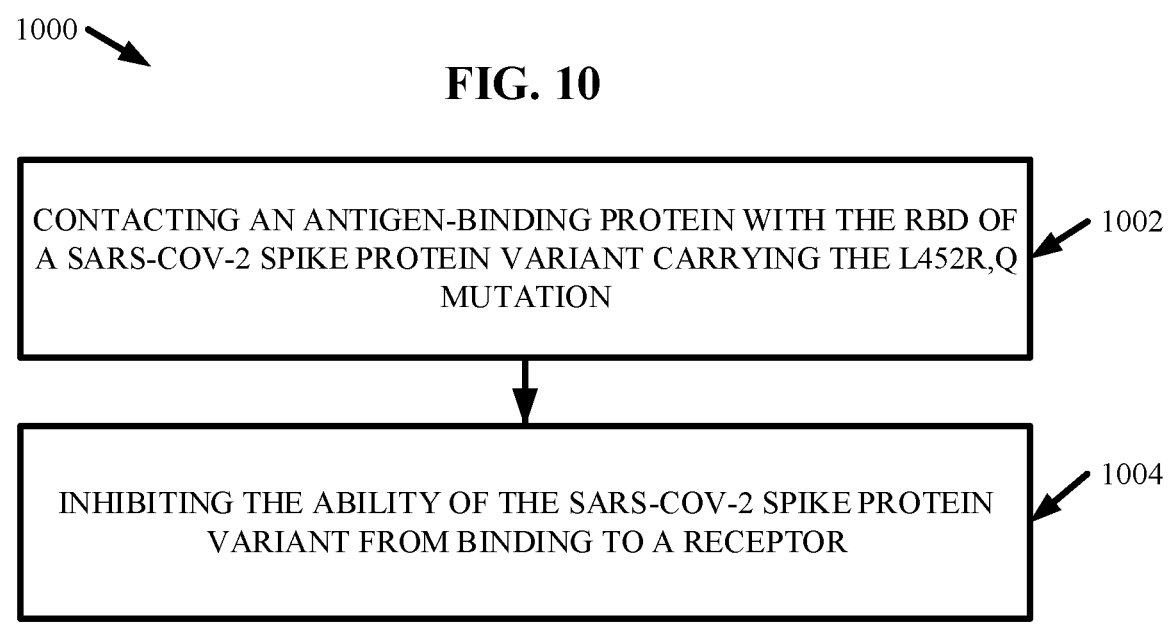

CONTACTING AN ANTIGEN-BINDING PROTEIN WITH THE RBD OF A SARS-COV-2 SPIKE PROTEIN VARIANT CARRYING THE L452R,Q MUTATION — 1002

INHIBITING THE ABILITY OF THE SARS-COV-2 SPIKE PROTEIN VARIANT FROM BINDING TO A RECEPTOR — 1004

ANTIGEN-BINDING PROTEINS TARGETING CORONAVIRUS (COV) VARIANTS

BACKGROUND

The subject disclosure relates to antigen-binding proteins, such as antibodies, single-domain antibodies (e.g., NANO-BODIES®) and/or antigen-binding fragments ("Fabs") thereof, that can bind to the spike protein of a CoV (e.g., SARS-CoV-2) variant, and more specifically, that can bind to the spike protein of a CoV (e.g., SARS-CoV-2) variant carrying the E484K,Q mutation and/or the L452R,Q mutation.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, molecules and/or methods regarding antigen-binding proteins that can inhibit the activity of CoV (e.g., SARS-CoV-2) are described.

According to an embodiment, an antigen-binding protein is provided. The antigen-binding protein can comprise a heavy polypeptide chain variable region with an amino acid sequence that is a variant of SEQ ID NO: 7. The amino acid sequence can comprise at least one amino acid substitution selected from the group consisting of: R50D, R50E, R50W, R50F, R50Y, R50L, R50V, R50I, R50Pho, I54D, I54E, I54W, I54F, I54Y, I54Pho, L55D, L55E, L55W, L55F, L55Y, and L55Pho.

According to another embodiment, an antigen-binding protein is provided. The antigen-binding protein can comprise a light polypeptide chain variable region with an amino acid sequence that is a variant of SEQ ID NO: 8. The amino acid sequence can comprise an amino acid substitution selected from the group consisting of: R96D, R96E, R96W, R96F, R96Y, R96L, R96V, R96I, and R96Pho.

According to another embodiment, an antigen-binding protein is provided. The antigen-binding protein can comprise a heavy polypeptide chain variable region with an amino acid sequence that is a variant of SEQ ID NO: 7. The amino acid sequence can comprise an amino acid substitution that substitutes at least one amino acid selected from the group consisting of R50, I54, and L55 with a negatively charged amino acid.

According to another embodiment, an antigen-binding protein is provided. The antigen-binding protein can comprise a heavy polypeptide chain variable region with an amino acid sequence that is a variant of SEQ ID NO: 7. The amino acid sequence can comprise an amino acid substitution that substitutes at least one amino acid selected from the group consisting of R50, I54, and L55 with a hydrophobic residue.

According to another embodiment, an antigen-binding protein is provided. The antigen-binding protein can comprise a heavy polypeptide chain variable region with an amino acid sequence that is a variant of SEQ ID NO: 7. The amino acid sequence can comprise an amino acid substitution that substitutes at least one amino acid selected from the group consisting of R50, I54, and L55 with an amino acid that forms a cation-π interaction with a receptor binding domain of a SARS-CoV-2 spike protein.

BRIEF DESCRIPTION OF THE DRAWINGS

FIG. 1 illustrates a diagram of example, non-limiting amino acid sequences of the RBD of a SARS-CoV-2 spike protein in accordance with one or more embodiments described herein.

FIG. 2 illustrates a diagram of an example, non-limiting amino acid sequence of the RBD of a SARS-CoV-2 spike protein carrying the L452R,Q amino acid substitution in accordance with one or more embodiments described herein.

FIG. 3 illustrates a diagram of an example, non-limiting amino acid sequence of the RBD of a SARS-CoV-2 spike protein carrying the E484K and L452R amino acid substitutions in accordance with one or more embodiments described herein.

FIG. 4 illustrates a diagram of example, non-limiting amino acid sequences of $V_H$ regions of a neutralizing antigen-binding protein with an amino acid substitution of the R50 amino acid in accordance with one or more embodiments described herein.

FIG. 5 illustrates a diagram of example, non-limiting amino acid sequences of $V_L$ regions of a neutralizing antigen-binding protein with an amino acid substitution of the R96 amino acid in accordance with one or more embodiments described herein.

FIG. 6 illustrates a diagram of example, non-limiting amino acid sequences of $V_H$ regions of a neutralizing antigen-binding protein with an amino acid substitution of the I54 amino acid in accordance with one or more embodiments described herein.

FIG. 7 illustrates a diagram of example, non-limiting amino acid sequences of $V_H$ regions of a neutralizing antigen-binding protein with an amino acid substitution of the L55 amino acid in accordance with one or more embodiments described herein.

FIG. 8 illustrates a diagram of an example, non-limiting table that can depict the binding free energy associated with various neutralizing antigen-binding proteins to demonstrate the efficacy the amino acid substitution described herein.

FIG. 10 illustrates a flow diagram of an example, non-limiting method that can be employed to inhibit the activity of a CoV (e.g., SARS-CoV-2) variant carrying the L452R,Q mutation in accordance with one or more embodiments described herein.

DETAILED DESCRIPTION

Figure 9:
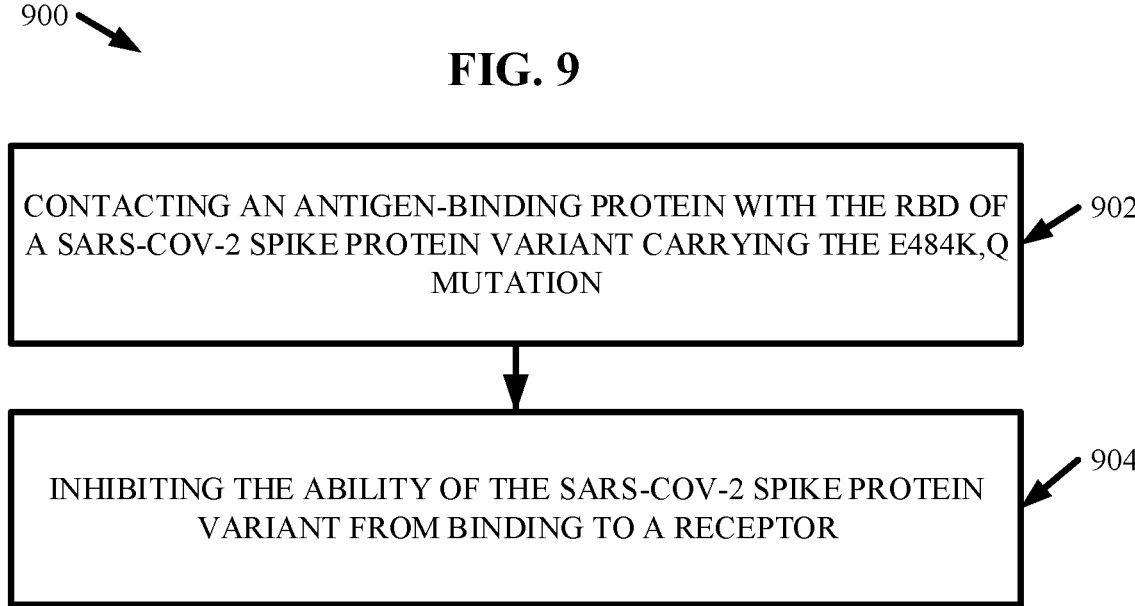
FIG. 9 illustrates a flow diagram of an example, non-limiting method that can be employed to inhibit the activity of a CoV (e.g., SARS-CoV-2) variant carrying the E484K,Q mutation in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

As used herein, the term "sequence identity" can refer to the relatedness between two amino acid sequences or between two nucleotide sequences. For example, the degree of sequence identity between two amino acid sequences can be determined using the Needleman-Wunsch algorithm. As used herein, the term "amino acid substitution" can refer to the replacement of one amino acid in an amino acid sequence with another amino acid. In various embodiments, the following nomenclature can be employed to define an amino acid substitution: [original amino acid][position of original amino acid in the amino acid sequence][substituted amino acid]. For example, the amino acid substitution E484K can delineate a replacement of glutamic acid (E) at the $484^{th}$ position of the given amino acid sequence with lysine (K). Further, amino acids can be referenced herein by their standard single letter code. Additionally, the following nomenclature can be employed to delineate an amino acid: [amino acid][position of amino acid in the amino acid sequence]. For example, the amino acid E484 can be the glutamic acid (E) at the $484^{th}$ position of the given amino acid sequence. Further, where a variant comprises a combination of amino acid substitutions, a "+" can be located between each respective amino acid substitution. Where different amino acids can be substituted at a given position, the possible substituents can be separated by a comma. For example, "R50D,E" can delineate two possible amino acid substitutions: R50D or R50E. Also, as used herein, the term "Pho" can represent a phosphorylated residue. For instance, an amino acid substitution comprising a phosphorylated residue can comprise an amino acid phosphorylated (e.g., via a post-translational modification ("PTM")). Example phosphorylated residues can include, but are not limited to: serine, threonine, and/or tyrosine.

As used herein, the term "coronavirus" and/or "CoV" refers to any virus of the coronavirus family, including but not limited to SARS-CoV-2, SARS-CoV-1, and/or Mers-Cov. As used herein, the term "SARS-CoV-2" refers to severe acute respiratory syndrome coronavirus 2 (SARS-CoV-2), which is a positive-sense single-stranded ribonucleic acid ("RNA") virus that causes the ongoing coronavirus disease 2019 ("COVID-19"). SARS-CoV-2 binds via a viral spike protein to human host cell receptor angiotensin-converting enzyme 2 ("ACE2"). The spike protein also binds to and is cleaved by TMPRSS2, which activates the spike protein for membrane fusion of the virus. The SARS-CoV-2 spike protein is a 1273 amino acid type I membrane glycoprotein which assembles into trimers that constitute the spikes or peplomers on the surface of the enveloped coronavirus particle. Further, the spike protein binds to its cognate receptor via a receptor binding domain ("RBD"). The amino acid sequence of the RBD of the SARS-CoV-2 spike protein can be defined by the amino acid sequence provided in SEQ ID NO: 1.

As used herein, the term "coronavirus infection" and/or "CoV infection," can refer to infection with a coronavirus such as SARS-CoV-2, SARS-CoV-1, and/or Mers-Cov. A coronavirus infection can include coronavirus respiratory tract infections, often in the lower respiratory tract. Symptoms can include high fever, dry cough, shortness of breath, pneumonia, gastro-intestinal symptoms such as diarrhea, organ failure (e.g., kidney failure and renal dysfunction), and/or the like.

As used herein, the term "antibody" can refer to immunoglobulin molecules comprising four polypeptide chains: two heavy polypeptide chains and two light polypeptide chains. Further, the heavy polypeptide chains can each comprise a heavy chain variable region ("$V_H$") and multiple heavy chain constant regions ("$C_H$"). Likewise, the light polypeptide chains can each comprise a light chain variable region ("$V_L$") and a light chain constant regions ("$C_L$"). As used herein, the term "antigen-binding fragment" ("Fab") can refer to the variable region and constant region of the heavy polypeptide chains and light polypeptide chains that bind to a target antigen (e.g., bind to the RBD of the SARS-Cov-2 spike protein. The Fab of an antibody can comprise at least one variable region, which can be of any size or amino acid composition. In Fabs having a $V_H$ associated with a $V_L$, the $V_H$ and $V_L$ can be situated relative to one another in any suitable arrangement. Alternatively, the Fab of an antibody can contain a monomeric $V_H$ or $V_L$. In various embodiments, the Fab can comprise at least one variable region covalently linked to at least one constant region. Moreover, Fabs described herein can comprise a homo-dimer or hetero-dimer (or other multimer) of any of the variable and constant region configurations. Further, in one or more embodiments, an antibody and/or Fab described herein can be conjugated to a moiety such a ligand or a therapeutic moiety ("immunoconjugate") (e.g., such as an anti-viral compound, a second anti-influenza antibody, or any other therapeutic moiety useful for treating a viral infection). Moreover, in one or more embodiments, an antibody and/or Fab thereof can be, for example, a chimeric antibody, hybrid antibody and/or recombinant antibody.

Various embodiments described herein can include monoclonal anti-CoV antigen-binding proteins (e.g., antibodies, single-domain antibodies (e.g., NANOBODIES®) and/or Fabs thereof) as well as monoclonal compositions comprising a plurality of isolated monoclonal antigen-binding proteins. As used herein, the term "monoclonal antibody" can refer to a population of substantially homogeneous antibodies. For example, the antibody molecules comprising a population of monoclonal antibodies can be substantially identical in amino acid sequence except for possible naturally occurring mutations that may be present in minor amounts.

As used herein, the terms "isolated antigen-binding proteins," "isolated antibodies," and/or "isolated Fabs" can refer to polypeptides, polynucleotides and/or vectors that are at least partially free of other biological molecules from the cells or cell culture from which they are produced. Such biological molecules include nucleic acids, proteins, single-domain antibodies (e.g., NANOBODIES®), other antibodies, lipids, carbohydrates, or other material such as cellular debris and growth medium. An isolated antibody and/or Fab can further be at least partially free of expression system components such as biological molecules from a host cell or of the growth medium thereof.

As used herein, the term "conservatively modified variant" and/or a "conservative substitution" refers to a variant wherein there is one or more substitutions of amino acids in a polypeptide with other amino acids having similar characteristics (e.g., charge, side-chain size, hydrophobicity/hydrophilicity, backbone conformation and rigidity, etc.). Such changes can be made without significantly disrupting the biological activity of the antibody or fragment. Those of skill in this art recognize that, in general, single amino acid substitutions in non-essential regions of a polypeptide do not substantially alter biological activity. In addition, substitutions of structurally or functionally similar amino acids can be less likely to significantly disrupt biological activity. Particularly, the variable regions (e.g., "$V_H$" and "$V_L$" in the heavy and light chains respectively) can be less conserved than the constant regions in a Fab. For example, mutations, such as amino acid substitutions, can be observed in the variable regions of the antigen-binding protein (e.g., antibodies, single-domain antibodies (e.g., NANOBODIES®) and/or Fabs thereof), which can allow the Fab to bind new targets. Also, as used herein, the term "neutralizing anti-CoV antigen-binding protein," can refer to a molecule (e.g., an antibody, a single-domain antibody (e.g., a NANOBODY®) and/or a Fab thereof) that can inhibit an activity of CoV to a detectable degree (e.g., can inhibit the ability of SARS-CoV-2 spike protein to bind to a receptor, such as ACE2).

Various embodiments described herein can regard neutralizing antigen-binding proteins that can bind to the RBD of one or more variants of the CoV spike protein. For example, the RBD of the SAR-COV-2 spike protein can span from the $333^{rd}$ to the $527^{th}$ position of the amino acid sequence of the SAR-COV-2 spike protein and can be delineated by the amino acid sequence shown in FIG. 1 as SEQ ID NO: 1. Repetitive description of like elements employed in other embodiments described herein is omitted for the sake of brevity. A first variant of the RBD of the SAR-COV-2 spike protein can comprise at least the amino acid substitution E484K, as shown in FIG. 1 as SEQ ID NO: 2. A second variant of the RBD of the SAR-COV-2 spike protein can comprise at least the amino acid substitution E484Q, as shown in FIG. 1 as SEQ ID NO: 3. A third variant of the RBD of the SAR-COV-2 spike protein can comprise at least the amino acid substitution L452R, as shown in FIG. 2 as SEQ ID NO: 4. Repetitive description of like elements employed in other embodiments described herein is omitted for the sake of brevity. A fourth variant of the RBD of the SAR-COV-2 spike protein can comprise at least the amino acid substitution L452Q, as shown in FIG. 2 as SEQ ID NO: 5. A fifth possible variant of the RBD of the SAR-COV-2 spike protein can comprise a combination of amino acid substitutions at E484 and L452, such as at least the amino acid sequence substitutions E484K and the L452R amino acid, as shown in FIG. 3 as SEQ ID NO: 6. Repetitive description of like elements employed in other embodiments described herein is omitted for the sake of brevity. One or more embodiments described herein can comprise neutralizing antigen-binding proteins (e.g., antibodies, single-domain antibodies (e.g., NANOBODIES®) and/or Fabs thereof) that can exhibit an affinity to bind to the first, second, third, fourth, and/or fifth variants of the RBD of the CoV (e.g., SAR-CoV-2) spike protein. For example, one or more embodiments described herein can comprise one or more neutralizing antigen-binding proteins (e.g., antibodies, single-domain antibodies (e.g., NANOBODIES®) and/or Fabs thereof) that can exhibit an affinity to bind to an RBD of CoV (e.g., SARS-CoV-2) spike protein having at least 50% sequence identity with SEQ ID NO: 2, SEQ ID NO: 3, SEQ ID NO: 4, SEQ ID NO: 5, and/or SEQ ID NO: 6.

The RBD of the CoV (e.g., SARS-CoV-2) spike protein (e.g., having the amino acid sequence of SEQ ID NO: 1) can bind strongly with a Fab of the Bamlanivimab antibody through two salt bridges. For example, the Fab of Bamlanivimab can have: a $V_H$ with the amino acid sequence of SEQ ID NO: 7 (e.g., shown in FIG. 4); and/or a $V_L$ with the amino acid sequence of SEQ ID NO: 8 (e.g., shown in FIG. 5). Repetitive description of like elements employed in other embodiments described herein is omitted for the sake of brevity. The E484 amino acid in SEQ ID NO: 1 (e.g., RBD of SARS-COV-2 spike protein) can form a salt bridge with the R50 amino acid in SEQ ID NO: 7 (e.g., $V_H$ of Bamlanivimab) and the R96 amino acid in SEQ ID NO: 8 (e.g., $V_L$ of Bamlanivimab). For instance, both the R50 and R96 amino acids of Bamlanivimab can be positively charged, whereas the E484 amino acid of the RBD of the SARS-CoV-2 spike protein can be negatively charged; thereby a local electrostatic interaction can be achieved via salt bridges formed simultaneous between: the R50 amino acid of Bamlanivimab and the E484 amino acid of the RBD of the SARS-CoV-2 spike protein; and the R96 amino acid of Bamlanivimab and the E484 amino acid of the RBD of the SARS-CoV-2 spike protein.

However, after the E484K,Q amino acid substitution in the RBD of a SARS-CoV-2 spike protein variant, the resulting positively charged lysine amino acid K484 or glutamine Q484 cannot coordinate with the R50 (e.g., of SEQ ID NO: 7) and/or R96 (e.g., of SEQ ID NO: 8) amino acids in the Fab of Bamlanivimab. The three positively charged residues (i.e., R50 amino acid of SEQ ID NO: 7, R96 amino acid of SEQ ID NO: 8, and K484 or Q484 amino acid of SEQ ID NO: 2, SEQ ID: 3 SEQ ID NO: 6) cannot achieve sufficient coordination due to at least electrostatic repulsion. For instance, the E484K amino acid substitution of SEQ ID NO: 2 and/or SEQ ID NO: 4 can increase the local binding free energy by, for example, 40.65 kilocalories per mol (kcal/mol); thereby destabilizing the interfacial interaction. Various embodiments described herein can regard amino acid substitutions to the Fab of Bamlanivimab (e.g., to SEQ ID NO: 7 and/or SEQ ID NO: 8) to enhance the binding affinity of the Fab of Bamlanivimab towards the K484 or Q484 amino acid of the RBD of the one or more SARS-CoV-2 spike protein variants (e.g., of SEQ ID NO: 2, SEQ ID NO: 3, and/or SEQ ID NO: 6).

For example, one or more embodiments described herein can comprise amino acid substations to the Fab of Bamlanivimab (e.g., to SEQ ID NO: 7 and/or SEQ ID NO: 8) in order to: form a salt bridge with the RBD of the one or more CoV (e.g., SARS-CoV-2) spike protein variants; incorporate a hydrophobic residue into the Fab to interact with the carbon chains of the RBD of the one or more CoV (e.g., SARS-CoV-2) spike protein variants; and/or establish cation-n interactions between the Fab and the RBD of the one or more CoV (e.g., SARS-CoV-2) spike protein variants.

For instance, one or more neutralizing antigen-binding proteins (e.g., antibodies, single-domain antibodies (e.g., NANOBODIES®) and/or Fabs thereof) can comprise one or more amino acid substitutions to the $V_H$ and/or $V_L$ of Bamlanivimab, substituting R50 of SEQ ID NO: 7 and/or R96 of SEQ ID NO: 8 with negatively charged aspartic acid (D) and/or glutamic acid (E). In another instance, one or more neutralizing antigen-binding proteins (e.g., antibodies, single-domain antibodies (e.g., NANOBODIES®) and/or Fabs thereof) can comprise one or more amino acid substitutions to the $V_H$ and/or $V_L$ of Bamlanivimab, substituting R50 of SEQ ID NO: 7 and/or R96 of SEQ ID NO: 8 with a hydrophobic amino acid, including, but not limited to: leucine (L), valine (V), and/or isoleucine (I). In a further instance, one or more neutralizing antigen-binding proteins (e.g., antibodies, single-domain antibodies (e.g., NANOBODIES®) and/or Fabs thereof) can comprise one or more amino acid substitutions to the $V_H$ and/or $V_L$ of Bamlanivimab, substituting R50 of SEQ ID NO: 7 and/or R96 of SEQ ID NO: 8 with tryptophan (W), phenylalanine (F), and/or tyrosine (Y) to establish cation-n interactions with the K484 or Q484 amino acid of the RBD of the one or more SARS-COV-2 spike protein variants (e.g., of SEQ ID NO: 2, SEQ ID NO: 3, and/or SEQ ID NO: 4).

For example, as shown in FIG. 4, various embodiments described herein can include a neutralizing antigen-binding protein (e.g., an antibody, a single-domain antibody (e.g., a NANOBODY® and/or a Fab thereof) comprising a $V_H$ with at least 50% sequence identity with SEQ ID NO: 7 and one of the following amino acid substitutions of SEQ ID NO: 7: R50D, R50E, R50W, R50F, R50Y, R50L, R50V, R50I, or R50Pho. For instance, various embodiments described herein can include a neutralizing antigen-binding protein (e.g., an antibody, a single-domain antibody (e.g., a NANO-BODY® and/or a Fab thereof) comprising a $V_H$ having at least at least 50% (e.g., at least 80%) sequence identity with one of the following amino acid sequences: SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16. The $V_L$ of the neutralizing antigen-binding protein can have an amino acid sequence having at least 50% sequence identity with SEQ ID NO: 8.

In another example, as shown in FIG. 5, various embodiments described herein can include a neutralizing antigen-binding protein (e.g., an antibody, a single-domain antibody (e.g., a NANOBODY® and/or a Fab thereof) comprising a $V_L$ with at least 50% sequence identity with SEQ ID NO: 8 and one of the following amino acid substitutions of SEQ ID NO: 8: R96D, R96E, R96W, R96F, R96Y, R96L, R96V, R96I, or R96Pho. For instance, various embodiments described herein can include a neutralizing antigen-binding protein (e.g., an antibody and/or Fab thereof) comprising a $V_L$ having at least 50% (e.g., at least 80%) sequence identity with one of the following amino acid sequences: SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. The $V_H$ of the neutralizing antigen-binding protein can have an amino acid sequence having at least 50% sequence identity with SEQ ID NO: 7.

In a further example, various embodiments described herein can include a neutralizing antigen-binding protein (e.g., an antibody, a single-domain antibody (e.g., a NANO-BODY® and/or a Fab thereof) comprising: a $V_H$ with at least 50% sequence identity with SEQ ID NO: 7 and one or more of the amino acid substitutions of SEQ ID NO: 7 described herein (e.g., R50D, R50E, R50W, R50F, R50Y, R50L, R50V, R50I, R50Pho); and a $V_L$ with at least 50% sequence identity with SEQ ID NO: 8 and one or more of the amino acid substitutions of SEQ ID NO: 8 described herein (e.g., R96D, R96E, R96W, R96F, R96Y, R96L, R96V, R96I, R96Pho). For instance, various embodiments described herein can include a neutralizing antigen-binding protein (e.g., an antibody, a single-domain antibody (e.g., a NANO-BODY® and/or a Fab thereof) comprising one of the following amino acid substitution combinations: R50D+R96D, R50D+R96E, R50D+R96W, R50D+R96F, R50D+R96Y, R50D+R96L, R50D+R96V, R50D+R96I, R50D+R96Pho, R50E+R96E, R50E+R96E, R50E+R96W, R50E+R96F, R50E+R96Y, R50E+R96L, R50E+R96V, R50E+R96I, R50E+R96Pho, R50W+R96D, R50W+R96E, R50W+R96W, R50W+R96F, R50W+R96Y, R50W+R96L, R50W+R96V, R50W+R96I, R50W+R96Pho, R50F+R96D, R50F+R96E, R50F+R96W, R50F+R96F, R50F+R96Y, R50F+R96L, R50F+R96V, R50F+R96I, R50F+R96Pho, R50Y+R96D, R50Y+R96E, R50Y+R96W, R50Y+R96F, R50Y+R96Y, R50Y+R96L, R50Y+R96V, R50Y+R96I, R50Y+R96Pho, R50L+R96D, R50L+R96E, R50L+R96W, R50L+R96F, R50L+R96Y, R50L+R96L, R50L+R96V, R50L+R96I, R50L+R96Pho, R50V+R96D, R50V+R96E, R50V+R96W, R50V+R96F, R50V+R96Y, R50V+R96L, R50V+R96V, R50V+R96I, R50V+R96Pho, R50I+R96D, R50I+R96E, R50I+R96W, R50I+R96F, R50I+R96Y, R50I+R96L, R50I+R96V, R50I+R96I, R50I+R96Pho, R50Pho+R96D, R50Pho+R96E, R50Pho+R96W, R50Pho+R96F, R50Pho+R96Y, R50Pho+R96L, R50Pho+R96V, R50Pho+R96I, R50Pho+R96Pho.

Additionally, various embodiments described herein can include one or more neutralizing antigen-binding proteins (e.g., antibodies, single-domain antibodies (e.g., NANO-BODIES® and/or Fabs thereof) having at least 50% sequence identity with Bamlanivimab's variable domain $V_H$ (e.g., defined by SEQ ID NO: 7), and comprising one or more amino acid substitutions with regards to the I54 and/or L55 amino acids of SEQ ID NO: 7. In one or more embodiments, one or more neutralizing antigen-binding proteins (e.g., antibodies, single-domain antibodies (e.g., NANOBODIES® and/or Fabs thereof) having at least 50% sequence identity with Bamlanivimab's variable domain $V_H$ (e.g., defined by SEQ ID NO: 7), and comprising one or more amino acid substitutions with regards to the I54 and/or L55 amino acids of SEQ ID NO: 7 can exhibit enhanced binding affinity for RBD variants of SARS-CoV-2 spike proteins carrying the amino acid substitution L452R,Q (e.g., for RBD of SARS-CoV-2 spike protein having the amino acid sequence of SEQ ID NO: 4, SEQ ID NO: 5, or SEQ ID NO: 6). For instance, after the L452R,Q mutation, the charged R452 or Q452 amino acid cannot coordinate well with the hydrophobic I54 and/or L55 amino acids.

For instance, one or more neutralizing antigen-binding proteins (e.g., antibodies, single-domain antibodies (e.g., NANOBODIES® and/or Fabs thereof) can comprise one or more amino acid substitutions to the $V_H$ of Bamlanivimab, substituting the I54 and/or L55 amino acids of SEQ ID NO: 7 with negatively charged aspartic acid (D) and/or glutamic acid (E). In another instance, one or more neutralizing antigen-binding proteins (e.g., antibodies and/or Fabs thereof) can comprise one or more amino acid substitutions to the $V_H$ of Bamlanivimab, substituting the I54 and/or L55 amino acids of SEQ ID NO: 7 with a negatively charged amino acid, including, but not limited to: D54, E54, D55, and/or E55. In a further instance, one or more neutralizing antigen-binding proteins (e.g., antibodies and/or Fabs thereof) can comprise one or more amino acid substitutions to the $V_H$ of Bamlanivimab, substituting the I54 and/or L55 amino acids of SEQ ID NO: 7 with tryptophan (W), phenylalanine (F), and/or tyrosine (Y) to establish cation-71 interactions with the R452 or Q452 amino acid of the RBD of the one or more SARS-CoV-2 spike protein variants (e.g., of SEQ ID NO: 4, SEQ ID NO: 5, and/or SEQ ID NO: 6).

For example, as shown in FIG. 6, various embodiments described herein can include a neutralizing antigen-binding protein (e.g., an antibody, an single-domain antibody (e.g., a NANOBODY® and/or a Fab thereof) comprising a $V_H$ with at least 50% sequence identity with SEQ ID NO: 7 and one of the following amino acid substitutions of SEQ ID NO: 7: I54D, I54E, I54W, I54F, I54Y, I54Pho. Repetitive description of like elements employed in other embodiments described herein is omitted for the sake of brevity. For instance, various embodiments described herein can include a neutralizing antigen-binding protein (e.g., an antibody, an single-domain antibody (e.g., a NANOBODY® and/or a Fab thereof) comprising a $V_H$ having at least 50% sequence identity with one of the following amino acid sequences: SEQ ID NO: 25, SEQ ID NO: 26, SEQ ID NO: 27, SEQ ID NO: 28, SEQ ID NO: 29. The $V_L$ of the neutralizing antigen-binding protein can have an amino acid sequence having at least 50% sequence identity with SEQ ID NO: 8, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another example, as shown in FIG. 7, various embodiments described herein can include a neutralizing antigen-binding protein (e.g., an antibody, an single-domain antibody (e.g., a NANOBODY® and/or a Fab thereof) comprising a $V_H$ with at least 50% sequence identity with SEQ ID NO: 7 and one of the following amino acid substitutions of SEQ ID NO: 7: L55D, L55E, L55W, L55F, L55Y, L55Pho. Repetitive description of like elements employed in other embodiments described herein is omitted for the sake of brevity. For instance, various embodiments described herein can include a neutralizing antigen-binding protein (e.g., an antibody, an single-domain antibody (e.g., a NANOBODY® and/or a Fab thereof) comprising a $V_H$ having at least 50% sequence identity with one of the following amino acid sequences: SEQ ID NO: 30, SEQ ID NO: 31, SEQ ID NO: 32, SEQ ID NO: 33, or SEQ ID NO: 34. The $V_L$ of the neutralizing antigen-binding protein can have an amino acid sequence having at least 50% sequence identity with SEQ ID NO: 8, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24.

In a further example, various embodiments described herein can include a neutralizing antigen-binding protein (e.g., an antibody, a single-domain antibody (e.g., a NANOBODY® and/or a Fab thereof) comprising a $V_H$ with a combination of two or more of the amino acid substitutions of SEQ ID NO: 7 described herein. For instance, various embodiments described herein can include one or more neutralizing antigen-binding proteins (e.g., antibodies, single-domain antibodies (e.g., NANOBODIES®) and/or Fabs thereof) having at least 50% sequence identity with SEQ ID NO: 7, and comprising one of the following amino acid substitution combinations: I54D+L55D, I54D+L55E, I54D+L55W, I54D+L55F, I54D+L55Y, I54D+L55Pho, I54E+L55D, I54E+L55E, I54E+L55W, I54E+L55F, I54E+L55Y, I54E+L55Pho, I54W+L55D, I54W+L55E, I54W+L55W, I54W+L55F, I54W+L55Y, I54W+L55Pho, I54F+L55D, I54F+L55E, I54F+L55W, I54F+L55F, I54F+L55Y, I54F+L55Pho, I54Y+L55D, I54Y+L55E, I54Y+L55W, I54Y+L55F, I54Y+L55Y, I54Y+L55Pho, I54Pho+L55D, I54Pho+L55E, I54Pho+L55W, I54Pho+L55F, I54Pho+L55Y, or I54Pho+L55Pho. In another instance, various embodiments described herein can include one or more neutralizing antigen-binding proteins (e.g., antibodies and/or Fabs thereof) having at least 50% sequence identity with SEQ ID NO: 7, and comprising one of the following amino acid substitution combinations: R50D+L55D, R50D+L55E, R50D+L55W, R50D+L55F, R50D+L55Y, R50D+L55Pho, R50E+L55D, R50E+L55E, R50E+L55W, R50E+L55F, R50E+L55Y, R50E+L55Pho, R50W+L55D, R50W+L55E, R50W+L55W, R50W+L55F, R50W+L55Y, R50W+L55Pho, R50F+L55D, R50F+L55E, R50F+L55W, R50F+L55F, R50F+L55Y, R50F+L55Pho, R50Y+L55D, R50Y+L55E, R50Y+L55W, R50Y+L55F, R50Y+L55Y, R50Y+L55Pho, R50Pho+L55D, R50Pho+L55E, R50Pho+L55W, R50Pho+L55F, R50Pho+L55Y, R50L+L55D, R50L+L55E, R50L+L55W, R50L+L55F, R50L+L55Y, R50V+L55D, R50V+L55E, R50V+L55W, R50V+L55F, R50V+L55Y, R50I+L55D, R50I+L55E, R50I+L55W, R50I+L55F, R50I+L55Y. In a further instance, various embodiments described herein can include one or more neutralizing antigen-binding proteins (e.g., antibodies and/or Fabs thereof) having at least 50% sequence identity with SEQ ID NO: 7, and comprising one of the following amino acid substitution combinations: I54D+R50D, I54D+R50E, I54D+R50W, I54D+R50F, I54D+R50Y, I54D+R50Pho, I54E+R50D, I54E+R50E, I54E+R50W, I54E+R50F, I54E+R50Y, I54E+R50Pho, I54W+R50D, I54W+R50E, I54W+R50W, I54W+R50F, I54W+R50Y, I54W+R50Pho, I54F+R50D, I54F+R50E, I54F+R50W, I54F+R50F, I54F+R50Y, I54F+R50Pho, I54Y+R50D, I54Y+R50E, I54Y+R50W, I54Y+R50F, I54Y+R50Y, I54Y+R50Pho, I54Pho+R50D, I54Pho+R50E, I54Pho+R50W, I54Pho+R50F, I54Pho+R50Y, or I54Pho+R50Pho. In an additional instance, various embodiments described herein can include one or more neutralizing antigen-binding proteins (e.g., antibodies and/or Fabs thereof) having at least 50% sequence identity with SEQ ID NO: 7, and comprising a combination of three amino acid substitutions of SEQ ID NO: 5 in accordance with: R50D,E,W, F,Y,Pho,L,V,I+I54D,E,W,F,Y,Pho+L55D,E,W,F,Y,Pho (e.g., such as R50D+I54D+L55D). Moreover, in each of the instances described above, the one or more neutralizing antigen-binding proteins can comprise a $V_L$ having the amino acid sequence of SEQ ID NO: 8, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

One or more embodiments described herein can include one or more neutralizing antigen-binding proteins (e.g., antibodies, single-domain antibodies (e.g., NANOBODIES®) and/or Fabs thereof) comprising: a $V_H$ with an amino acid sequence having at least 50% sequence identity with SEQ ID NO: 10 (e.g., comprising the amino acid substitution R50E of SEQ ID NO: 7), and a $V_L$ with an amino acid sequence having at least 50% sequence identity with SEQ ID NO: 18 (e.g., comprising the amino acid substitution R96E of SEQ ID NO: 8). For example, the K484 amino acid of the RBD variant of SARS-CoV-2 spike protein having SEQ ID NO: 2 or SEQ ID NO: 6 (e.g., carrying the E484K amino acid substitution) can form a first salt bridge with the E50 amino acid (e.g., comprised within the $V_H$) and/or a second salt bridge with the E96 amino acid (e.g., comprised within the $V_L$) of the one or more neutralizing antigen-binding proteins (e.g., antibodies and/or Fabs thereof). At least because the E50 and E96 amino acids of the neutralizing antigen-binding protein can be negatively charged, the K484 amino acid of the RBD of the SARS-CoV-2 spike protein can electrostatically favor the interaction with the E50 and E96 amino acids.

Table 1, shown in FIG. 8, depicts protein-protein interaction energies calculated via molecular mechanics-generalized Born surface area ("MMGBSA"). Repetitive description of like elements employed in other embodiments described herein is omitted for the sake of brevity. In Table 1: "RBD-E484 (WT)" represents a SARS-CoV-2 spike protein comprising an RBD with the amino acid sequence of SEQ ID NO: 1; "RBD-K484" represents a SARS-CoV-2 spike protein comprising an RBD with the amino acid sequence of SEQ ID NO: 2; and "Bamlanivimab-EE" represents an antigen-binding protein (e.g., a variant of Bamlanivimab) comprising a $V_H$ with an amino acid sequence having at least 50% sequence identity with of SEQ ID NO: 10 (e.g., comprising the amino acid substitution R50E of SEQ ID NO: 7), and a $V_L$ with an amino acid sequence having at least 50% sequence identity with SEQ ID NO: 18 (e.g., comprising the amino acid substitution R96E of SEQ ID NO: 8) in accordance with various embodiments described herein. As shown in Table 1, the binding free energy for a complex of Bamlanivimab and the SARS-CoV-2 spike protein comprising a RBD having the amino acid sequence of SEQ ID NO: 1 can be −157.87 kcal/mol. However, after the E484K mutation, the binding free energy can increase to −108.24 kcal/mol (e.g., suggesting that the interfacial interaction is substantially weakened. In contrast, the binding free energy for a complex of an antigen-binding protein (e.g., a variant of Bamlanivimab) comprising a $V_H$ with an amino acid sequence having at least 50% sequence identity with SEQ ID NO: 10 (e.g., comprising the amino acid substitution R50E of SEQ ID NO: 7), and a $V_L$ with an amino acid sequence having at least 50% sequence identity with SEQ ID NO: 18 (e.g., comprising the amino acid substitution R96E of SEQ ID NO: 8) and the SARS-CoV-2 spike protein carrying the E484K mutation can be −156.79 kcal/mol; thereby demonstrating that the various neutralizing antigen-binding proteins (e.g., antibodies, single-domain antibodies (e.g., NANOBODIES®) and/or Fabs thereof) can achieve a binding affinity towards the SARS-CoV-2 variant that is comparable to that between Bamlanivimab and the RBD of the SARS-CoV-2 nonvariant.

One or more embodiments described herein can include one or more neutralizing antigen-binding proteins (e.g., antibodies, single-domain antibodies (e.g., NANOBOD-IES®) and/or Fabs thereof) comprising: a $V_H$ with an amino acid sequence having at least 50% sequence identity with SEQ ID NO: 10 (e.g., comprising the amino acid substitution R50E of SEQ ID NO: 7), and a $V_L$ with an amino acid sequence having at least 50% sequence identity with SEQ ID NO: 19 (e.g., comprising the amino acid substitution R96W of SEQ ID NO: 8). For example, the K484 amino acid of the RBD variant of SARS-CoV-2 spike protein having SEQ ID NO: 2 or SEQ ID NO: 6 (e.g., carrying the E484K amino acid substitution) can form a salt bridge with the E50 amino acid (e.g., comprised within the $V_H$) and/or favorable cation-71 interactions with the W96 amino acid (e.g., comprised within the $V_L$) of the one or more neutralizing antigen-binding proteins (e.g., antibodies, single-domain antibodies (e.g., NANOBODIES®) and/or Fabs thereof).

In one or more embodiments, the various neutralizing antigen-binding proteins described herein can be isolated antibodies. In various embodiments, the $V_H$ and/or $V_L$ regions described herein can be conservatively modified variants of the example amino acid sequences. For example, conservatively modified variants of SEQ ID NO: 9-SEQ ID NO: 34. Additionally, in accordance with the various embodiments described herein, the various neutralizing antigen-binding proteins described herein can be included in one or more therapeutic compounds. For example, the one or more neutralizing antigen-binding proteins can be included in a composition with a pharmaceutically acceptable carrier and/or other therapeutic agent (e.g., an anti-inflammatory agent, an antibody that binds to TMPRSS2, and/or an antibody that binds to the SARS-CoV-2 spike protein). In another example, the one or more neutralizing antigen-binding proteins described herein can be included in one or more combination therapies (e.g., therapies that further include Bamlanivimab, remdesivir, and/or dexamethasone).

FIG. 9 illustrates a flow diagram of an example, non-limiting method 900 that can facilitate treating a CoV infection with one or more neutralizing antigen-binding proteins (e.g., antibodies, single-domain antibodies (e.g., NANOBODIES®) and/or Fabs thereof) in accordance with one or more embodiments described herein. Repetitive description of like elements employed in other embodiments described herein is omitted for the sake of brevity. In various embodiments, method 900 can be employed to facilitate treatment of a CoV infection comprising SARS-CoV-2 carrying the E484K,Q mutation.

At 902, the method 900 can comprise contacting one or more antigen-binding proteins with the RBD of a SARS-CoV-2 spike protein variant carrying the E484K,Q mutation.

For example, the RBD of the SARS-CoV-2 spike protein variant can have the amino acid sequence of SEQ ID NO: 2 or SEQ ID NO: 6. In various embodiments, the one or more antigen-binding proteins can comprise a variant of Bamla-nivimab's $V_H$ and/or $V_L$ regions, and can comprise one or more amino acid substitutions of the R50, I54, L55, and/or R96 amino acids in accordance with various embodiments described herein. For instance, the one or more antigen-binding proteins can be a variant of Bamlanivimab's $V_H$ and/or $V_L$ regions comprising one or more amino acid substitutions of the R50 and/or R96 amino acids with: one or more negatively charged amino acids (e.g., D and/or E), one or more hydrophobic residues (e.g., L, V, and/or I), one or more phosphorylated residues (e.g., serine, threonine, or tyrosine), and/or one or more molecules (e.g., amino acids W, F, and/or Y) that can establish cation-71 interactions with the RBD.

In various embodiments, the contacting at 902 can be facilitated by administering an effective concentration (e.g., 35 milligrams per milliliter (mg/mL)) of the one or more antigen-binding proteins to a patient inflicted with a CoV infection. For example, the one or more antigen-binding proteins can be included in one or more therapeutic compositions (e.g., comprising a pharmaceutically acceptable carrier) that can be injected into the patient via a needle.

At 904, the method 900 can comprise inhibiting the ability of the SARS-CoV-2 spike protein variant from binding to a receptor. For example, the one or more antigen-binding proteins can inhibit the SARS-CoV-2 spike protein variant from binding to receptor ACE2. For instance, the one or more antigen-binding proteins can form one or more salt bridges with the RBD of the SARS-CoV-2 spike protein variant to facilitate the inhibiting at 904. In another instance, one or more hydrophobic residues of the one or more antigen-binding proteins can interact with one or more carbon chains of K484 in the RBD of the SARS-CoV-2 spike protein variant to facilitate the inhibiting at 904. In a further instance, the one or more antigen-binding proteins can form one or more cation-n interactions with the RBD of the SARS-CoV-2 spike protein variant to facilitate the inhibiting at 904.

FIG. 10 illustrates a flow diagram of an example, non-limiting method 1000 that can facilitate treating a CoV infection with one or more neutralizing antigen-binding proteins (e.g., antibodies, single-domain antibodies (e.g., NANOBODIES®) and/or Fabs thereof) in accordance with one or more embodiments described herein. Repetitive description of like elements employed in other embodiments described herein is omitted for the sake of brevity. In various embodiments, method 1000 can be employed to facilitate treatment of a CoV infection comprising SARS-CoV-2 carrying the L452R,Q mutation.

At 1002, the method 1000 can comprise contacting one or more antigen-binding proteins with the RBD of a SARS-CoV-2 spike protein variant carrying the L452R,Q mutation. For example, the RBD of the SARS-CoV-2 spike protein variant can have the amino acid sequence of SEQ ID NO: 3, SEQ ID NO: 4, or SEQ ID NO: 6. In various embodiments, the one or more antigen-binding proteins can be a variant of Bamlanivimab's $V_H$ and/or $V_L$ regions (e.g., be a variant of Bamlanivimab), and can comprise one or more amino acid substitutions of the R50, I54, L55, and/or R96 amino acids in accordance with various embodiments described herein. For instance, the one or more antigen-binding proteins can comprise variant of Bamlanivimab's $V_H$ and/or $V_L$ regions (e.g., be a variant of Bamlanivimab) comprising one or more amino acid substitutions of the I54, L55, and/or R96 amino acids with: one or more negatively charged amino acids (e.g., D and/or E), one or more hydrophobic residues (e.g., L, V, or I), one or more phosphorylated residues (e.g., serine, threonine, or tyrosine), and/or one or more molecules (e.g., amino acids W, F, and/or Y) that can establish cation-n interactions with the RBD.

In various embodiments, the contacting at 1002 can be facilitated by administering an effective concentration (e.g., 35 milligrams per milliliter (mg/mL)) of the one or more antigen-binding proteins to a patient inflicted with a CoV infection. For example, the one or more antigen-binding proteins can be included in one or more therapeutic compositions (e.g., comprising a pharmaceutically acceptable carrier) that can be injected into the patient via a needle.

At 1004, the method 1000 can comprise inhibiting the ability of the SARS-CoV-2 spike protein variant from binding to a receptor. For example, the one or more antigen-binding proteins can inhibit the SARS-CoV-2 spike protein variant from binding to receptor ACE2. For instance, the one or more antigen-binding proteins can form one or more salt bridges with the RBD of the SARS-CoV-2 spike protein variant to facilitate the inhibiting at 1004. In another instance, one or more hydrophobic residues of the one or more antigen-binding proteins can interact with one or more carbon chains of the RBD of the SARS-CoV-2 spike protein variant to facilitate the inhibiting at 1004. In a further instance, the one or more antigen-binding proteins can form one or more cation-n interactions with the RBD of the SARS-CoV-2 spike protein variant to facilitate the inhibiting at 1004.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

---

What is claimed is:

1. An antigen-binding protein, comprising:
   a heavy polypeptide chain variable region with a first amino acid sequence that comprises SEQ ID NO: 10; and
   a light polypeptide chain variable region with a second amino acid sequence that is selected from the first group consisting of SEQ ID NO: 18 and SEQ ID NO: 19.

2. The antigen-binding protein of claim 1, wherein the heavy polypeptide chain variable region and the light polypeptide chain variable region have a binding interaction with a portion of a receptor binding domain of a variant of a SARS-CoV-2 spike protein.

3. The antigen-binding protein of claim 2, wherein the binding interaction is relative to an amino acid substitution of the receptor binding domain of the variant of the SARS-CoV-2 spike protein.

4. The antigen-binding protein of claim 3, wherein the binding interaction comprises formation of a salt-bridge.

5. The antigen-binding protein of claim 3, wherein the binding interaction comprises a cation-n interaction.

6. An antigen-binding protein, comprising:
   a heavy polypeptide chain variable region with a first amino acid sequence that comprises SEQ ID NO: 10; and
   a light polypeptide chain variable region with a second amino acid sequence that comprises SEQ ID NO: 18.

7. The antigen-binding protein of claim 6, wherein the heavy polypeptide chain variable region and the light poly-peptide chain variable region have a binding interaction with a portion of a receptor binding domain of a variant of a SARS-CoV-2 spike protein.

8. The antigen-binding protein of claim 7, wherein the binding interaction is relative to an amino acid substitution of the receptor binding domain of the variant of the SARS-CoV-2 spike protein.

9. The antigen-binding protein of claim 8, wherein the binding interaction comprises formation of a salt-bridge.

10. An antigen-binding protein, comprising:
   a heavy polypeptide chain variable region with a first amino acid sequence that comprises SEQ ID NO: 10; and
   a light polypeptide chain variable region with a second amino acid sequence that comprises SEQ ID NO: 19.

11. The antigen-binding protein of claim 10, wherein the heavy polypeptide chain variable region and the light poly-peptide chain variable region have a binding interaction with a portion of a receptor binding domain of a variant of a SARS-CoV-2 spike protein.

12. The antigen-binding protein of claim 11, wherein the binding interaction is relative to an amino acid substitution of the receptor binding domain of the variant of the SARS-CoV-2 spike protein.

13. The antigen-binding protein of claim 11, wherein the binding interaction comprises formation of a salt-bridge.

14. The antigen-binding protein of claim 11, wherein the binding interaction comprises a cation-π interaction.

* * * * *

SEQUENCE LISTING

```
<160> NUMBER OF SEQ ID NOS: 34

<210> SEQ ID NO 1
<211> LENGTH: 195
<212> TYPE: PRT
<213> ORGANISM: SARS-CoV-2
<220> FEATURE:
<221> NAME/KEY: DOMAIN
<222> LOCATION: (1)..(195)
<223> OTHER INFORMATION: Receptor-binding domain of spike protein

<400> SEQUENCE: 1

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
                100                 105                 110
```

-continued

```
Val Gly Gly Asn Tyr Asn Tyr Leu Tyr Arg Leu Phe Arg Lys Ser Asn
        115                 120                 125

Leu Lys Pro Phe Glu Arg Asp Ile Ser Thr Glu Ile Tyr Gln Ala Gly
        130                 135                 140

Ser Thr Pro Cys Asn Gly Val Glu Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
                180                 185                 190

Cys Gly Pro
        195

<210> SEQ ID NO 2
<211> LENGTH: 195
<212> TYPE: PRT
<213> ORGANISM: SARS-CoV-2
<220> FEATURE:
<221> NAME/KEY: DOMAIN
<222> LOCATION: (1)..(195)
<223> OTHER INFORMATION: Receptor-binding domain of spike protein
<220> FEATURE:
<221> NAME/KEY: VARIANT
<222> LOCATION: (152)..(152)
<223> OTHER INFORMATION: Variant of SARS-CoV-2 with E484K substitution

<400> SEQUENCE: 2

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
                20                  25                  30

Tyr Ser Val Leu Tyr Asn Ser Ala Ser Phe Ser Thr Phe Lys Cys Tyr
            35                  40                  45

Gly Val Ser Pro Thr Lys Leu Asn Asp Leu Cys Phe Thr Asn Val Tyr
        50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
            100                 105                 110

Val Gly Gly Asn Tyr Asn Tyr Leu Tyr Arg Leu Phe Arg Lys Ser Asn
        115                 120                 125

Leu Lys Pro Phe Glu Arg Asp Ile Ser Thr Glu Ile Tyr Gln Ala Gly
        130                 135                 140

Ser Thr Pro Cys Asn Gly Val Lys Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
                180                 185                 190

Cys Gly Pro
        195

<210> SEQ ID NO 3
<211> LENGTH: 195
<212> TYPE: PRT
<213> ORGANISM: SARS-CoV-2
```

-continued

```
<220> FEATURE:
<221> NAME/KEY: DOMAIN
<222> LOCATION: (1)..(195)
<223> OTHER INFORMATION: Receptor-binding domain of spike protein
<220> FEATURE:
<221> NAME/KEY: VARIANT
<222> LOCATION: (152)..(152)
<223> OTHER INFORMATION: Variant of SARS-CoV-2 with E484Q substitution

<400> SEQUENCE: 3

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
                100                 105                 110

Val Gly Gly Asn Tyr Asn Tyr Leu Tyr Arg Leu Phe Arg Lys Ser Asn
        115                 120                 125

Leu Lys Pro Phe Glu Arg Asp Ile Ser Thr Glu Ile Tyr Gln Ala Gly
    130                 135                 140

Ser Thr Pro Cys Asn Gly Val Gln Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
                180                 185                 190

Cys Gly Pro
        195

<210> SEQ ID NO 4
<211> LENGTH: 195
<212> TYPE: PRT
<213> ORGANISM: SARS-CoV-2
<220> FEATURE:
<221> NAME/KEY: DOMAIN
<222> LOCATION: (1)..(195)
<223> OTHER INFORMATION: Receptor-binding domain of spike protein
<220> FEATURE:
<221> NAME/KEY: VARIANT
<222> LOCATION: (120)..(120)
<223> OTHER INFORMATION: Variant of SARS-CoV-2 with L452R substitution

<400> SEQUENCE: 4

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
```

-continued

```
65                    70                    75                    80

Gly Gln Thr Gly Lys Ile Ala Asp Tyr Asn Tyr Lys Leu Pro Asp Asp
                    85                    90                    95

Phe Thr Gly Cys Val Ile Ala Trp Asn Ser Asn Asn Leu Asp Ser Lys
                100                   105                   110

Val Gly Gly Asn Tyr Asn Tyr Arg Tyr Arg Leu Phe Arg Lys Ser Asn
            115                   120                   125

Leu Lys Pro Phe Glu Arg Asp Ile Ser Thr Glu Ile Tyr Gln Ala Gly
        130                   135                   140

Ser Thr Pro Cys Asn Gly Val Glu Gly Phe Asn Cys Tyr Phe Pro Leu
145                   150                   155                   160

Gln Ser Tyr Gly Phe Gln Pro Thr Asn Gly Val Gly Tyr Gln Pro Tyr
                165                   170                   175

Arg Val Val Val Leu Ser Phe Glu Leu Leu His Ala Pro Ala Thr Val
                180                   185                   190

Cys Gly Pro
        195
```

```
<210> SEQ ID NO 5
<211> LENGTH: 195
<212> TYPE: PRT
<213> ORGANISM: SARS-CoV-2
<220> FEATURE:
<221> NAME/KEY: DOMAIN
<222> LOCATION: (1)..(195)
<223> OTHER INFORMATION: Receptor-binding domain of spike protein
<220> FEATURE:
<221> NAME/KEY: VARIANT
<222> LOCATION: (120)..(120)
<223> OTHER INFORMATION: Variant of SARS-CoV-2 with L452Q substitution

<400> SEQUENCE: 5

Thr Asn Leu Cys Pro Phe Gly Glu Val Phe Asn Ala Thr Arg Phe Ala
1               5                   10                    15

Ser Val Tyr Ala Trp Asn Arg Lys Arg Ile Ser Asn Cys Val Ala Asp
                20                    25                    30

Tyr Ser Val Leu Tyr Asn Ser Ala Ser Phe Ser Thr Phe Lys Cys Tyr
            35                    40                    45

Gly Val Ser Pro Thr Lys Leu Asn Asp Leu Cys Phe Thr Asn Val Tyr
        50                    55                    60

Ala Asp Ser Phe Val Ile Arg Gly Asp Glu Val Arg Gln Ile Ala Pro
65                    70                    75                    80

Gly Gln Thr Gly Lys Ile Ala Asp Tyr Asn Tyr Lys Leu Pro Asp Asp
                85                    90                    95

Phe Thr Gly Cys Val Ile Ala Trp Asn Ser Asn Asn Leu Asp Ser Lys
                100                   105                   110

Val Gly Gly Asn Tyr Asn Tyr Gln Tyr Arg Leu Phe Arg Lys Ser Asn
            115                   120                   125

Leu Lys Pro Phe Glu Arg Asp Ile Ser Thr Glu Ile Tyr Gln Ala Gly
        130                   135                   140

Ser Thr Pro Cys Asn Gly Val Glu Gly Phe Asn Cys Tyr Phe Pro Leu
145                   150                   155                   160

Gln Ser Tyr Gly Phe Gln Pro Thr Asn Gly Val Gly Tyr Gln Pro Tyr
                165                   170                   175

Arg Val Val Val Leu Ser Phe Glu Leu Leu His Ala Pro Ala Thr Val
                180                   185                   190

Cys Gly Pro
```

-continued

```
        195
```

```
<210> SEQ ID NO 6
<211> LENGTH: 195
<212> TYPE: PRT
<213> ORGANISM: SARS-CoV-2
<220> FEATURE:
<221> NAME/KEY: DOMAIN
<222> LOCATION: (1)..(195)
<223> OTHER INFORMATION: Receptor-binding domain of spike protein
<220> FEATURE:
<221> NAME/KEY: VARIANT
<222> LOCATION: (120)..(120)
<223> OTHER INFORMATION: Variant of SARS-CoV-2 with L452R substitution
<220> FEATURE:
<221> NAME/KEY: VARIANT
<222> LOCATION: (152)..(152)
<223> OTHER INFORMATION: Variant of SARS-CoV-2 with E484K substitution

<400> SEQUENCE: 6

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
            100                 105                 110

Val Gly Gly Asn Tyr Asn Tyr Arg Tyr Arg Leu Phe Arg Lys Ser Asn
        115                 120                 125

Leu Lys Pro Phe Glu Arg Asp Ile Ser Thr Glu Ile Tyr Gln Ala Gly
    130                 135                 140

Ser Thr Pro Cys Asn Gly Val Lys Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
            180                 185                 190

Cys Gly Pro
        195

<210> SEQ ID NO 7
<211> LENGTH: 229
<212> TYPE: PRT
<213> ORGANISM: Artificial Sequence
<220> FEATURE:
<223> OTHER INFORMATION: Heavy Polypeptide Chain Variable Region of
    Bamlanivimab

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
```

```
              35                    40                    45
Gly Arg Ile Ile Pro Ile Leu Gly Ile Ala Asn Tyr Ala Gln Lys Phe
        50                    55                    60
Gln Gly Arg Val Thr Ile Thr Ala Asp Lys Ser Thr Ser Thr Ala Tyr
65                    70                    75                    80
Met Glu Leu Ser Ser Leu Arg Ser Glu Asp Thr Ala Val Tyr Tyr Cys
                    85                    90                    95
Ala Arg Gly Tyr Tyr Glu Ala Arg His Tyr Tyr Tyr Tyr Ala Met
              100                   105                   110
Asp Val Trp Gly Gln Gly Thr Ala Val Thr Val Ser Ser Ala Ser Thr
              115                   120                   125
Lys Gly Pro Ser Val Phe Pro Leu Ala Pro Cys Ser Arg Ser Thr Ser
        130                   135                   140
Glu Ser Thr Ala Ala Leu Gly Cys Leu Val Lys Asp Tyr Phe Pro Glu
145                   150                   155                   160
Pro Val Thr Val Ser Trp Asn Ser Gly Ala Leu Thr Ser Gly Val His
              165                   170                   175
Thr Phe Pro Ala Val Leu Gln Ser Ser Gly Leu Tyr Ser Leu Ser Ser
              180                   185                   190
Val Val Thr Val Pro Ser Ser Ser Leu Gly Thr Lys Thr Tyr Thr Cys
              195                   200                   205
Asn Val Asp His Lys Pro Ser Asn Thr Lys Val Asp Lys Arg Val His
        210                   215                   220
His His His His His
225
```

<210> SEQ ID NO 8
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab

<400> SEQUENCE: 8

```
Asp Ile Gln Met Thr Gln Ser Pro Ser Ser Leu Ser Ala Ser Val Gly
1                     5                    10                    15
Asp Arg Val Thr Ile Thr Cys Arg Ala Ser Gln Ser Ile Ser Ser Tyr
              20                    25                    30
Leu Ser Trp Tyr Gln Gln Lys Pro Gly Lys Ala Pro Lys Leu Leu Ile
        35                    40                    45
Tyr Ala Ala Ser Ser Leu Gln Ser Gly Val Pro Ser Arg Phe Ser Gly
        50                    55                    60
Ser Gly Ser Gly Thr Asp Phe Thr Leu Thr Ile Thr Ser Leu Gln Pro
65                    70                    75                    80
Glu Asp Phe Ala Thr Tyr Tyr Cys Gln Gln Ser Tyr Ser Thr Pro Arg
                    85                    90                    95
Thr Phe Gly Gln Gly Thr Lys Val Glu Ile Lys Arg Thr Val Ala Ala
              100                   105                   110
Pro Ser Val Phe Ile Phe Pro Pro Ser Asp Glu Gln Leu Lys Ser Gly
              115                   120                   125
Thr Ala Ser Val Val Cys Leu Leu Asn Asn Phe Tyr Pro Arg Glu Ala
        130                   135                   140
Lys Val Gln Trp Lys Val Asp Asn Ala Leu Gln Ser Gly Asn Ser Gln
145                   150                   155                   160
```

-continued

```
Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr Gln Gly Thr Thr Ser Val Thr Lys Ser Phe Asn
        195             200             205

Arg Gly Glu Cys
    210

<210> SEQ ID NO 9
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50D Mutagen

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Asp Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Tyr Tyr Glu Ala Arg His Tyr Tyr Tyr Tyr Ala Met
            100             105             110

Asp Val Trp Gly Gln Gly Thr Ala Val Thr Val Ser Ser Ala Ser Thr
            115             120             125

Lys Gly Pro Ser Val Phe Pro Leu Ala Pro Cys Ser Arg Ser Thr Ser
    130             135             140

Glu Ser Thr Ala Ala Leu Gly Cys Leu Val Lys Asp Tyr Phe Pro Glu
145             150             155             160

Pro Val Thr Val Ser Trp Asn Ser Gly Ala Leu Thr Ser Gly Val His
            165             170             175

Thr Phe Pro Ala Val Leu Gln Ser Ser Gly Leu Tyr Ser Leu Ser Ser
            180             185             190

Val Val Thr Val Pro Ser Ser Ser Leu Gly Thr Lys Thr Tyr Thr Cys
        195             200             205

Asn Val Asp His Lys Pro Ser Asn Thr Lys Val Asp Lys Arg Val His
    210             215             220

His His His His His
225

<210> SEQ ID NO 10
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50E Mutagen

<400> SEQUENCE: 10
```

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Glu Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val His
    210                 215                 220

His His His His His
225
```

```
<210> SEQ ID NO 11
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50W Mutagen

<400> SEQUENCE: 11
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Trp Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
        115                 120                 125
```

-continued

```
Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val His
    210                 215                 220

His His His His His
225
```

```
<210> SEQ ID NO 12
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50F Mutagen

<400> SEQUENCE: 12
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Phe Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val His
    210                 215                 220

His His His His His
225
```

-continued

<210> SEQ ID NO 13
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50Y Mutagen

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Tyr Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val His
    210                 215                 220

His His His His His
225

<210> SEQ ID NO 14
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50L Mutagen

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Leu Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr

```
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val His
    210                 215                 220

His His His His His
225
```

```
<210> SEQ ID NO 15
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50V Mutagen

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Val Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

-continued

```
Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val His
        210                 215                 220

His His His His His
225

<210> SEQ ID NO 16
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with R50I Mutagen

<400> SEQUENCE: 16

Gln Val Gln Leu Val Gln Ser Gly Ala Glu Val Lys Lys Pro Gly Ser
1                 5                   10                  15

Ser Val Lys Val Ser Cys Lys Ala Ser Gly Gly Thr Phe Ser Asn Tyr
        20                  25                  30

Ala Ile Ser Trp Val Arg Gln Ala Pro Gly Gln Gly Leu Glu Trp Met
        35                  40                  45

Gly Ile Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
        115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val His
        210                 215                 220

His His His His His
225

<210> SEQ ID NO 17
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96D Mutagen

<400> SEQUENCE: 17

Asp Ile Gln Met Thr Gln Ser Pro Ser Ser Leu Ser Ala Ser Val Gly
1                 5                   10                  15
```

```
Asp Arg Val Thr Ile Thr Cys Arg Ala Ser Gln Ser Ile Ser Ser Tyr
        20                  25                  30

Leu Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Asp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr Gln Gly Thr Thr Ser Val Thr Lys Ser Phe Asn
                195                 200                 205

Arg Gly Glu Cys
        210
```

```
<210> SEQ ID NO 18
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96E Mutagen

<400> SEQUENCE: 18
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
        20                  25                  30

Leu Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Glu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr Gln Gly Thr Thr Ser Val Thr Lys Ser Phe Asn
        195                 200                 205

Arg Gly Glu Cys
        210
```

```
<210> SEQ ID NO 19
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96W Mutagen

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr Gln Gly Thr Thr Ser Val Thr Lys Ser Phe Asn
        195                 200                 205

Arg Gly Glu Cys
        210
```

```
<210> SEQ ID NO 20
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96F Mutagen

<400> SEQUENCE: 20

Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr Gln Gly Thr Thr Ser Val Thr Lys Ser Phe Asn
        195                 200                 205

Arg Gly Glu Cys
    210

<210> SEQ ID NO 21
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96Y Mutagen

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln

-continued

```
145                150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
                180                185                190

Ala Cys Glu Val Thr Gln Gly Thr Thr Ser Val Thr Lys Ser Phe Asn
                195                200                205

Arg Gly Glu Cys
        210

<210> SEQ ID NO 22
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96L Mutagen

<400> SEQUENCE: 22

Asp Ile Gln Met Thr Gln Ser Pro Ser Ser Leu Ser Ala Ser Val Gly
1                5                10                15

Asp Arg Val Thr Ile Thr Cys Arg Ala Ser Gln Ser Ile Ser Ser Tyr
                20                25                30

Leu Ser Trp Tyr Gln Gln Lys Pro Gly Lys Ala Pro Lys Leu Leu Ile
                35                40                45

Tyr Ala Ala Ser Ser Leu Gln Ser Gly Val Pro Ser Arg Phe Ser Gly
        50                55                60

Ser Gly Ser Gly Thr Asp Phe Thr Leu Thr Ile Thr Ser Leu Gln Pro
65                70                75                80

Glu Asp Phe Ala Thr Tyr Tyr Cys Gln Gln Ser Tyr Ser Thr Pro Leu
                85                90                95

Thr Phe Gly Gln Gly Thr Lys Val Glu Ile Lys Arg Thr Val Ala Ala
                100                105                110

Pro Ser Val Phe Ile Phe Pro Pro Ser Asp Glu Gln Leu Lys Ser Gly
        115                120                125

Thr Ala Ser Val Val Cys Leu Leu Asn Asn Phe Tyr Pro Arg Glu Ala
        130                135                140

Lys Val Gln Trp Lys Val Asp Asn Ala Leu Gln Ser Gly Asn Ser Gln
145                150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
                180                185                190

Ala Cys Glu Val Thr Gln Gly Thr Thr Ser Val Thr Lys Ser Phe Asn
                195                200                205

Arg Gly Glu Cys
        210

<210> SEQ ID NO 23
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96V Mutagen

<400> SEQUENCE: 23

Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Val
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr Gln Gly Thr Thr Ser Val Thr Lys Ser Phe Asn
        195                 200                 205

Arg Gly Glu Cys
    210
```

```
<210> SEQ ID NO 24
<211> LENGTH: 212
<212> TYPE: PRT
<213> ORGANISM: Artificial Sequence
<220> FEATURE:
<223> OTHER INFORMATION: Light Polypeptide Chain Variable Region of
      Bamlanivimab with R96I Mutagen

<400> SEQUENCE: 24
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ser Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

-continued

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr Gln Gly Thr Thr Ser Val Thr Lys Ser Phe Asn
        195                 200                 205

Arg Gly Glu Cys
    210

<210> SEQ ID NO 25
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with I54D Mutagen
<220> FEATURE:
<221> NAME/KEY: MUTAGEN
<222> LOCATION: (54)..(54)
<223> OTHER INFORMATION: I54D

<400> SEQUENCE: 25

Gln Val Gln Leu Val Gln Ser Gly Ala Glu Val Lys Lys Pro Gly Ser
1                   5                   10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Arg Ile Ile Pro Asp Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val His
    210                 215                 220

His His His His His
225

<210> SEQ ID NO 26
<211> LENGTH: 229
<212> TYPE: PRT

<213> ORGANISM: Artificial Sequence
<220> FEATURE:
<223> OTHER INFORMATION: Heavy Polypeptide Chain Variable Region of
      Bamlanivimab with I54E Mutagen

<400> SEQUENCE: 26

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Glu Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val His
    210                 215                 220

His His His His His
225
```

<210> SEQ ID NO 27
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with I54W Mutagen

<400> SEQUENCE: 27

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Trp Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
```

-continued

```
                    85                  90                  95
Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
                195                 200                 205

Asn Val Asp His Lys Pro Ser Asn Thr Lys Val Asp Lys Arg Val His
        210                 215                 220

His His His His His
225
```

```
<210> SEQ ID NO 28
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with I54F Mutagen

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
            35                  40                  45

Gly Arg Ile Ile Pro Phe Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
                195                 200                 205
```

Asn Val Asp His Lys Pro Ser Asn Thr Lys Val Asp Lys Arg Val His
    210                 215                 220

His His His His His
225

<210> SEQ ID NO 29
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with I54Y Mutagen

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Tyr Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val His
    210                 215                 220

His His His His His
225

<210> SEQ ID NO 30
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with L55D Mutagen

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

-continued

```
Ala Ile Ser Trp Val Arg Gln Ala Pro Gly Gln Gly Leu Glu Trp Met
    35                  40                  45

Gly Arg Ile Ile Pro Ile Asp Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val His
    210                 215                 220

His His His His His
225
```

```
<210> SEQ ID NO 31
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with L55E Mutagen

<400> SEQUENCE: 31
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
    35                  40                  45

Gly Arg Ile Ile Pro Ile Glu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160
```

-continued

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val His
    210                 215                 220

His His His His His
225
```

```
<210> SEQ ID NO 32
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with L55W Mutagen

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
            35                  40                  45

Gly Arg Ile Ile Pro Ile Trp Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val His
    210                 215                 220

His His His His His
225
```

```
<210> SEQ ID NO 33
<211> LENGTH: 229
<212> TYPE: PRT
<213> ORGANISM: Artificial Sequence
<220> FEATURE:
<223> OTHER INFORMATION: Heavy Polypeptide Chain Variable Region of
```

-continued

Bamlanivimab with L55F Mutagen

<400> SEQUENCE: 33

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Ala Met
            100                 105                 110

Asp Val Trp Gly Gln Gly Thr Ala Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val His
    210                 215                 220

His His His His His
225
```

<210> SEQ ID NO 34
<211> LENGTH: 229
<212> TYPE: PRT
<213> ORGANISM: Artificial Sequence
<220> FEATURE:
<223> OTHER INFORMATION: Heavy Polypeptide Chain Variable Region of
      Bamlanivimab with L55Y Mutagen

<400> SEQUENCE: 34

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Arg Ile Ile Pro Ile Tyr Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Glu Ala Arg His Tyr Tyr Tyr Tyr Tyr Ala Met
```

-continued

```
             100                 105                 110

Asp Val Trp Gly Gln Gly Thr Ala Val Thr Val Ser Ser Ala Ser Thr
        115             120             125

Lys Gly Pro Ser Val Phe Pro Leu Ala Pro Cys Ser Arg Ser Thr Ser
    130             135             140

Glu Ser Thr Ala Ala Leu Gly Cys Leu Val Lys Asp Tyr Phe Pro Glu
145             150             155             160

Pro Val Thr Val Ser Trp Asn Ser Gly Ala Leu Thr Ser Gly Val His
            165             170             175

Thr Phe Pro Ala Val Leu Gln Ser Ser Gly Leu Tyr Ser Leu Ser Ser
            180             185             190

Val Val Thr Val Pro Ser Ser Ser Leu Gly Thr Lys Thr Tyr Thr Cys
        195             200             205

Asn Val Asp His Lys Pro Ser Asn Thr Lys Val Asp Lys Arg Val His
    210             215             220

His His His His His
225
```